(12) United States Patent
Kim et al.

(10) Patent No.: US 7,629,583 B2
(45) Date of Patent: Dec. 8, 2009

(54) METHOD AND APPARATUS FOR ANALYZING A PHOTORESIST FILM

(75) Inventors: Young-Hoon Kim, Gyeonggi-do (KR);
Hong Lee, Gyeonggi-do (KR);
Youn-Kyung Wang, Gyeonggi-do (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 11/938,402

(22) Filed: Nov. 12, 2007

(65) Prior Publication Data

US 2008/0117408 A1    May 22, 2008

(30) Foreign Application Priority Data

Nov. 16, 2006   (KR)   .................. 10-2006-0113067

(51) Int. Cl.
*G01J 5/02* (2006.01)
(52) U.S. Cl. .................. 250/339.07; 250/341.4
(58) Field of Classification Search ............ 250/339.07, 250/339.08, 341.1, 341.4, 372, 580, 341.6
See application file for complete search history.

(56) References Cited

U.S. PATENT DOCUMENTS 6,030,266 A * 2/2000 Ida et al. .................... 445/24
6,385,294 B2 * 5/2002 Suzuki et al. ............... 378/136

FOREIGN PATENT DOCUMENTS

| JP | 09-265189 | | 10/1997 |
| JP | 09265189 A | * | 10/1997 |
| KR | 10-2004-0095554 A | | 11/2004 |
| KR | 0547279 | | 1/2006 |

* cited by examiner

*Primary Examiner*—David P Porta
*Assistant Examiner*—David S Baker
(74) *Attorney, Agent, or Firm*—Myers Bigel Sibley & Sajovec, P.A.

(57) ABSTRACT

In a method for analyzing photoresist, light having a wavelength which responds to a photoresist film is selected. The photoresist film is exposed to the selected light. Changes of components and properties of the photoresist film are analyzed while the photoresist film is being exposed to the selected light.

4 Claims, 3 Drawing Sheets

METHOD AND APPARATUS FOR ANALYZING A PHOTORESIST FILM

CROSS-REFERENCE TO RELATED APPLICATION

This application claims priority under 35 USC § 119 to Korean Patent Application No. 2006-113067, filed on Nov. 16, 2006 in the Korean Intellectual Property Office (KIPO), the contents of which are incorporated herein by reference in their entirety.

FIELD OF THE INVENTION

The present invention relates generally to semiconductor devices and, more particularly to semiconductor device manufacturing.

BACKGROUND OF THE INVENTION

A process for manufacturing a semiconductor device may require fine photoresist patterns for forming fine patterns because of strict design rules. To form the fine photoresist patterns, a photoresist film having low optical absorbance and high photosensitivity may be required. For the photoresist film, changes and properties of components in the photoresist film are analyzed when the photoresist film is exposed.

Fourier transform infrared spectroscopy (FT-IR) is generally used for analyzing properties of a material. Spectrums showing the properties of the material may be easily acquired using FT-IR. In addition, the molecular structure of the material may be identified because spectrums of all materials, except for optical isomers, are different from one another.

However, to analyze the changes and properties of the photoresist film, an apparatus for exposing the photoresist film may be required. Thus, the changes and properties of the photoresist film may not be analyzed using only FT-IR.

SUMMARY

Example embodiments of the present invention provide a method of analyzing photoresist film that is capable of analyzing changes and properties of components in a photoresist film during an exposure process.

Example embodiments of the present invention also provide an apparatus for performing the above-mentioned method.

According to one embodiment of the present invention, there is provided a method of analyzing a photoresist film. In the method of analyzing the photoresist film, light having a wavelength, which is responsive to the photoresist film in accordance with the type of the photoresist film, is selected. The selected light is irradiated to the photoresist film to expose the photoresist film. Changes and properties of components in the photoresist film are analyzed while the photoresist film is exposed to the selected light.

The light may include a laser beam in an ultraviolet range, or an X-ray. When the laser beam is selected as the light, a laser source gas, which is used for exposing the photoresist film, among a plurality of laser source gases may be selected. Examples of the laser source gases may include, but are not limited to, argon fluoride (ArF) gas, krypton fluoride (KrF) gas, and fluorine (F2) gas.

The changes and properties of the components of the photoresist film may be analyzed by irradiating the photoresist film with infrared light, by detecting the infrared light passing through the photoresist film, and by processing the detection results.

According to the method of analyzing the photoresist film, the light for exposing the photoresist film may be selected and irradiated in accordance with the type of the photoresist film. Thus, various types of the photoresist films may be analyzed using the present method.

According to one embodiment of the present invention, there is provided an apparatus for analyzing a photoresist film. The apparatus for analyzing the photoresist film includes a light generator, a controller and an infrared spectroscope. The light generator generates light having various wavelengths and irradiates the generated light onto the photoresist film. The controller selects light having a wavelength, which is responsive to the photoresist film, in accordance with the type of the photoresist film. The infrared spectroscope analyzes changes and properties of the components in the photoresist film caused by exposing the photoresist film to the selected light. The infrared spectroscope includes an infrared ray source for irradiating an infrared ray to the photoresist film, a detector for detecting the infrared ray passing through the photoresist film, and a processor for processing the detection results of the detector and outputting processed results.

In some embodiments of the present invention, the light generator may include a laser generating unit and an X-ray generating unit. The laser generating unit generates laser beams having wavelengths in an ultraviolet range. The X-ray generating unit generates X-ray beams.

In some embodiments of the present invention, the laser generating unit may include a plurality of gas storage parts, a laser beam generating part and a selecting part. The gas storage parts may store a plurality of laser source gases. The laser beam generating part may generate the laser beams using the laser source gases and irradiate the laser beams onto the photoresist film. The selecting part may be arranged between the gas storage parts and laser beam generating part to selectively provide the laser beam generating part with one of the laser source gases. The gas storage parts may separately store argon fluoride (ArF) gas, krypton fluoride (KrF) gas and fluorine (F2) gas.

In some embodiments of the present invention, the X-ray generating unit may include a cathode, a grid electrode and a target. The cathode may emit thermo-electrons. The grid electrode may control the thermo-electrons emitted from the cathode. The target may generate an X-ray when the thermo-electrons are caused to collide against the target.

In some embodiments of the present invention, the light generator may further include a control unit for controlling a path of light generated by the laser generating unit to irradiate the light to only the photoresist film.

According to some embodiments of the present invention, the apparatus for analyzing the photoresist film may selectively irradiate one of ultraviolet light and an X-ray light onto a photoresist film. Thus, various types of photoresist films may be analyzed using the present apparatus.

BRIEF DESCRIPTION OF THE DRAWINGS

The above and other features and advantages of the present invention will become readily apparent by reference to the following detailed description when considered in conjunction with the accompanying drawings wherein.

DESCRIPTION OF EMBODIMENTS

Figure 1:
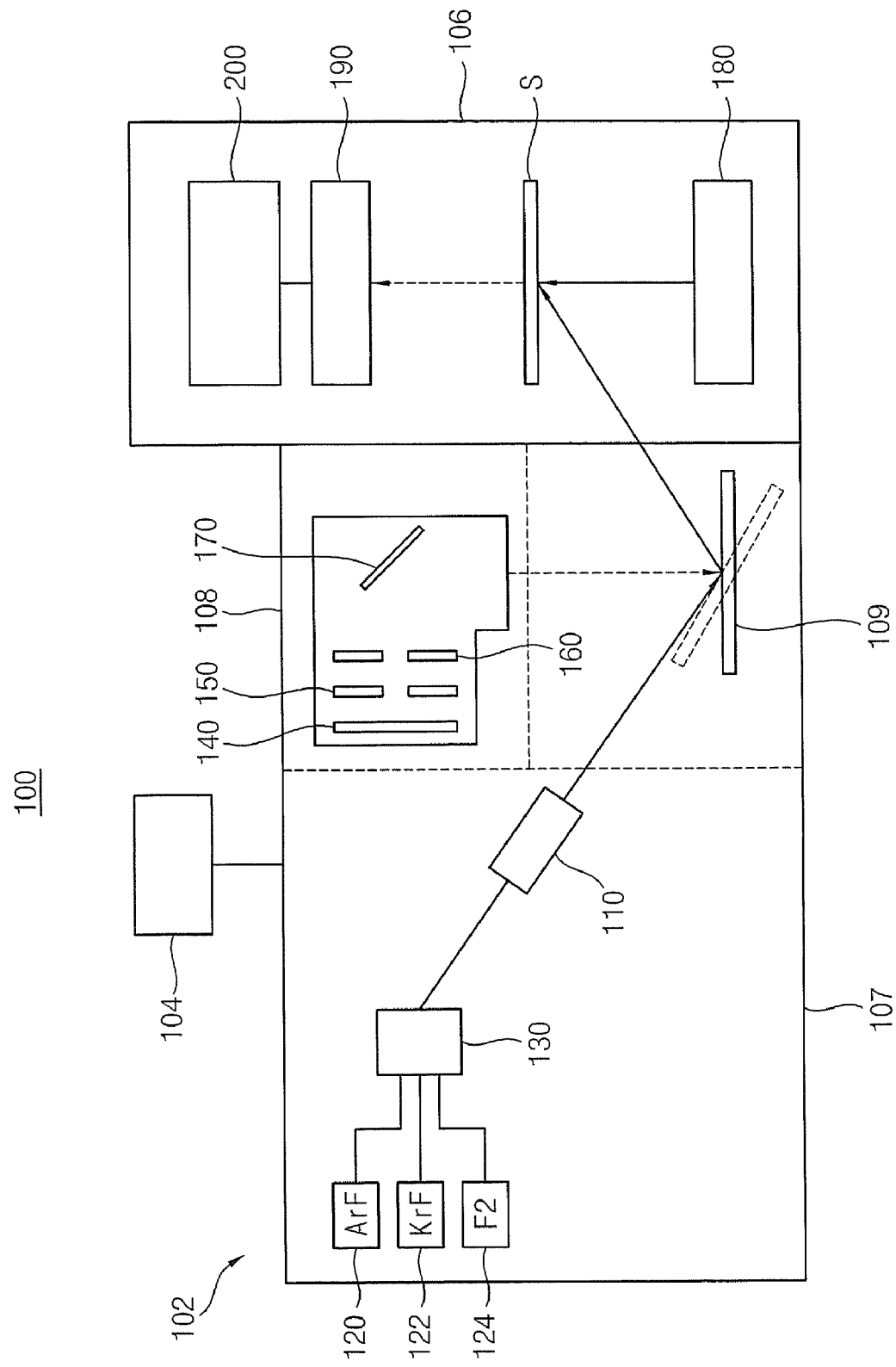
FIG. 1 is a block diagram illustrating an apparatus for analyzing a photoresist film in accordance with some embodiments of the present invention.

The present invention is described more fully hereinafter with reference to the accompanying drawings, in which example embodiments of the present invention are shown. The present invention may, however, be embodied in many different forms and should not be construed as limited to the example embodiments set forth herein. Rather, these example embodiments are provided so that this disclosure will be thorough and complete, and will fully convey the scope of the present invention to those skilled in the art. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like reference numerals refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments of the present invention are described herein with reference to cross-section illustrations that are schematic illustrations of idealized embodiments (and intermediate structures) of the present invention. As such, variations from the shapes of the illustrations as a result, for example, of manufacturing techniques and/or tolerances, are to be expected. Thus, example embodiments of the present invention should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1 is a block diagram illustrating an apparatus for analyzing a photoresist film in accordance with some embodiments of the present invention.

Referring to FIG. 1, an apparatus 100 for analyzing a photoresist film includes a light generator 102, a controller 104 and an infrared spectroscope 106. The light generator 102 generates light. For example, the light may include ultraviolet rays and/or X-rays. The light generated by the light generator 102 is irradiated onto a photoresist film S. The controller 104 selects light having a wavelength, which is responsive to the photoresist film, in accordance with the type of the photoresist film and controls the light generator to generate the selected light. The infrared spectroscope 106 analyzes changes and properties of components in the photoresist film S which are caused by the light irradiated onto the photoresist film S. For example, the infrared spectroscope 106 receives infrared light passing through the photoresist film S to analyze changes of a molecular structure or arrangement of the photoresist film S which is caused by the light irradiated to the photoresist film S and properties of the photoresist film S having the changed molecular structure or arrangement.

The photoresist film may include a photo-acid generator compound that is sensitive to light. The photoresist film may include one of a positive photoresist material and a negative photoresist material. A portion of the positive photoresist material exposed to the light is removed by a developing solution. Alternately, a portion of the negative photoresist material, which is not exposed to the light, is removed by the developing solution.

The light generator 102 includes a laser generating unit 107, an X-ray generating unit 108 and a control unit 109. The laser generating unit 107 generates ultraviolet rays. The X-ray generating unit 108 generates X-rays. The control unit 109 controls a path of light generated by the laser generating unit 107 and/or the X-ray generating unit 108 so that the light generated by the laser generating unit 107 and/or the X-ray generating unit 108 is irradiated onto only the photoresist film S.

The laser generating unit 107 includes a laser beam source 110, a first gas storage unit 120, a second gas storage unit 122, a third gas storage unit 124, and a selecting part 130 which may include one or more valves configured to selectively provide gas from the first, second, and third gas storage units 120, 122, 124 to the laser beam source 110.

The laser beam source 110 generates laser beams using a source gas. In some embodiments of the present invention, the laser beam source 110 may include a discharge tube, a mirror and a half-mirror. The discharge tube is provided with a high voltage by a power supply. The mirror is disposed at a first end of the discharge tube. The half-mirror is disposed at a second end of the discharge tube opposite to the first end. The source gas is injected into the discharge tube. Electrons of the source gas injected into the discharge tube are excited when the high voltage is applied to the discharge tube. Light having a predetermined wavelength is generated when the excited electrons of the source gas return to a stable state. The light having the predetermined wavelength is reflected by the mirror and the half-mirror so that the light moves between the mirror and the half-mirror. The half-mirror reflects some light and transmits the remaining light so that the light transmitted by the half-mirror is emitted from the laser beam source 110.

The first, second and third gas storage units 120, 122 and 124 are connected to the laser beam source 110 and provide the laser beam source 110 with the respective source gases. For example, the first gas storage unit 120 may provide the laser beam source 110 with krypton fluoride (KrF) gas as the source gas. The laser beam source 110 generates laser beams having a wavelength of about 284 nm when the krypton fluoride (KrF) gas serves as the source gas. For example, the second gas storage unit 122 may provide the laser beam source 110 with argon fluoride (ArF) gas as the source gas. The laser beam source 110 generates laser beams having a wavelength of about 193 nm when the argon fluoride (ArF) gas serves as the source gas. For example, the third gas storage unit 124 may provide the laser beam source 110 with fluorine (F2) gas as the source gas. The laser beam source 110 generates laser beams having a wavelength of about 157 nm when the fluorine (F2) gas serves as the source gas.

The selecting part 130 is connected to lines connecting first, second and third gas storage units 120, 122 and 124 with the laser beam source 110. The selecting part 130 selectively opens one of the lines connecting the first, second and third gas storage units 120, 122 and 124 with the laser beam source 110 so that the laser beam source 110 generates light having a wavelength in an ultraviolet ray range, when the photoresist film S includes a photoresist material that is responsive to ultraviolet light. Thus, one of the krypton fluoride (KrF) gas, the argon fluoride (ArF) gas and the fluorine (F2) gas is selectively provided to the laser beam source 110.

The X-ray generating unit 108 includes a cathode part 140, a grid electrode part 150, a focus electrode part 160, and a target part 170.

The cathode part 140 emits electrons. In some embodiments of the present invention, the cathode part 140 may receive heat to emit the electrons. In other embodiments of the present invention, the cathode part 140 may receive a high voltage to emit the electrons. The grid electrode part 150 accelerates the electrons emitted from the cathode part 140. The focus electrode part 160 concentrates the accelerated electrons. The concentrated electrons hit the target part 170. X-ray beams and heat may be generated when the electrons hit the target part 170. The X-ray beams are emitted from the X-ray generating unit 108 through a window formed in a surface of the X-ray generating unit 108 which faces the control unit 109.

The control unit 109 controls a path of light generated by the laser generating unit 107 or the X-ray generating unit 109 so that the light generated by the laser generating unit 107 or the X-ray generating unit 109 is irradiated onto only the photoresist film S. Laser beams generated by the laser generating unit 107 and X-ray beams generated by the X-ray generating unit 109 have high intensity so that an infrared source part 180 and a detecting part 190 of the infrared spectroscope 106 may be damaged when the laser beams or the X-ray beams are directly irradiated onto the infrared source part 180 and the detecting part 190. Thus, the control unit 109 may prevent damage to the infrared source part 180 and the detecting part 190 by preventing laser beams generated by the laser generating unit 107 and x-ray beams generated by the x-ray generating unit 109 from irradiating the infrared source part 180 and detecting part 190. In some embodiments of the present invention, the control unit 109 may include a mirror.

The controller 104 is connected to the light generator 102 and controls the light generator 102 so that the light generator 102 generates light having a wavelength, which is responsive to the photoresist film S. In some embodiments of the present invention, the controller 104 is connected to the laser generating unit 107 and the X-ray generating unit 108. The controller 104 may control the laser generating unit 107 so that the laser generating unit 107 generates laser beams when the photoresist film S is responsive to light having a wavelength in an ultraviolet range. For example, the controller 104 may control the selecting part 130 so that the laser generating unit 107 generates the laser beams having the wavelength which is responsive to the photoresist film S. In some embodiments of the present invention, the controller may control the X-ray generating unit 108 so that the X-ray generating unit 108 generates X-ray beams when the photoresist film S is responsive to the X-ray beams.

The infrared spectroscope 106 includes the infrared source part 180, the detecting part 190 and a processing part 200.

The infrared source part 180 irradiates infrared light onto the photoresist film S. For example, the infrared source part 180 may irradiate the infrared light onto a surface of the photoresist film S onto which the laser beams or the X-ray beams generated by the light generator 102 are irradiated.

In some embodiments of the present invention, a concentrating lens and an interferometer may be disposed between the infrared source part 180 and the photoresist film S. For example, the interferometer may include a Michelson interferometer. However, various types of interferometers may be utilized.

The detecting part 190 is disposed opposite to the infrared source part 180 with respect to the photoresist film S, as illustrated in FIG. 1, and detects infrared light passing through the photoresist film S.

The processing part 200 is connected to the detecting part 190. The processing part 200 processes operations in response to output signals provided from the detecting part 190, and displays processed results. For example, the processed results may be displayed in a graph form. Examples of the processing part 200 may include a computer.

Atoms of the photoresist film S ordinarily vibrate at a basic frequency. The basic frequency may be in a frequency range of infrared light. Thus, the atoms of the photoresist film S absorb infrared energy so that the amplitude of vibration of the atoms may be increased, when the infrared spectroscope 106 irradiates the infrared light having a frequency which is the same as the basic frequency onto the photoresist film S. Therefore, the molecular structure of the photoresist film S may be analyzed by detecting changes of transmissivity of the infrared light passing through the photoresist film S.

The apparatus 100 for analyzing the photoresist film simultaneously processes an exposure of the photoresist film S and analysis of the photoresist film S. That is, the apparatus 100 for analyzing the photoresist film instantly analyzes changes and properties of components in the photoresist film S caused by exposing the photoresist film S to the laser beams or the X-ray beams.

Figure 2:
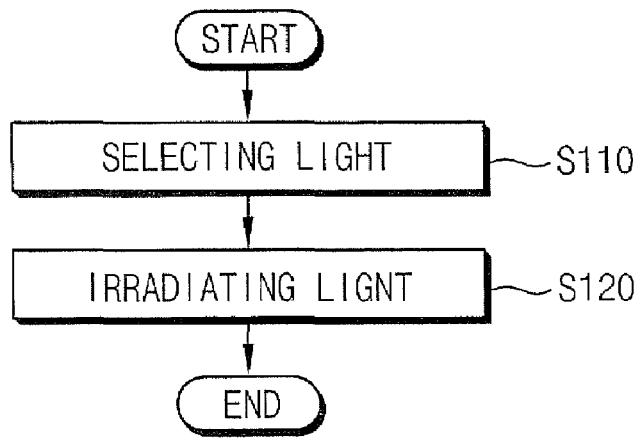
FIGS. 2 to 4 are flow charts illustrating a method of analyzing a photoresist film in accordance with some embodiments of the present invention.
Figure 3:
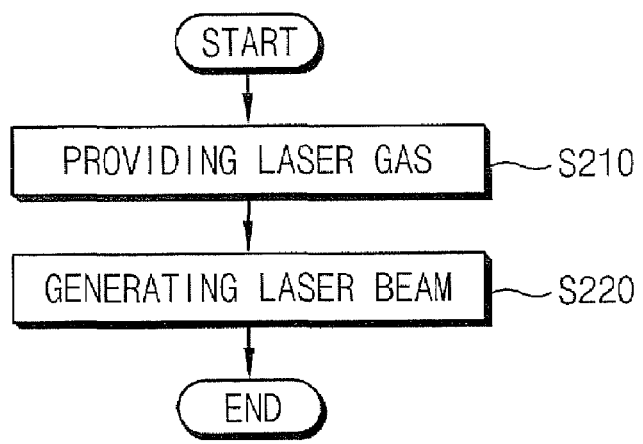
Figure 4:
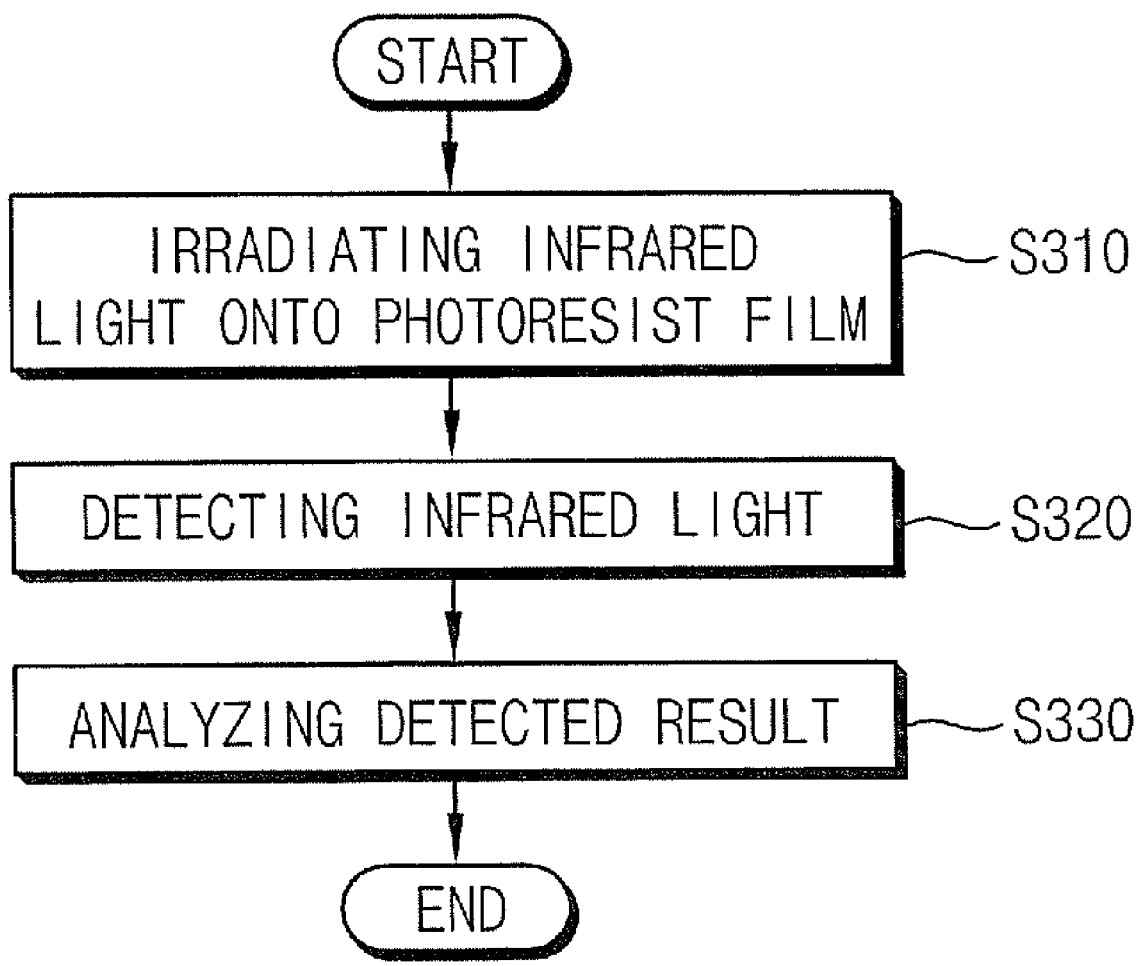

FIG. 2 is a flow chart illustrating a method of analyzing a photoresist film, according to some embodiments of the present invention. FIG. 3 is a flow chart illustrating a step of irradiating laser beams onto the photoresist film, according to some embodiments of the present invention. FIG. 4 is a flow chart illustrating a step of analyzing the photoresist film shown in FIG. 2, according to some embodiments of the present invention.

Referring to FIG. 2, the photoresist film S is disposed on a path of the infrared light generated from the infrared spectroscope 106. A type of light that is to be generated from the light generator 102 is selected in accordance with the type of the photoresist film S (step S110).

In some embodiments of the present invention, either the laser beams or the X-ray beams are selected in consideration of a wavelength region of light which is responsive to the photoresist film S. For example, a laser beam having a first wavelength in an ultraviolet range may be selected when the photoresist film S is responsive to ultraviolet light having the first wavelength. Alternatively, an X-ray beam may be selected when the photoresist film S is responsive to the X-ray beam.

The selected light is generated and the generated light is irradiated onto the photoresist film, after the type of the light has been selected (step S120).

Referring to FIG. 3, when the photoresist film is responsive to a laser beam, the selecting part 130 provides the laser beam source 110 with the source gas via the controller 104, so that the laser beam source 110 generates the laser beam (step S210).

In some embodiments of the present invention, the selecting part 130 may provide the laser beam source 110 with the krypton fluoride (KrF) gas stored in the first gas storage unit 120 when the photoresist film S is responsive to a laser beam having a wavelength of about 248 nm. In some embodiments of the present invention, the selecting part 130 may provide the laser beam source 110 with argon fluoride (ArF) gas stored in the second gas storage unit 122 when the photoresist film S is responsive to a laser beam having a wavelength of about 193 nm. In some embodiments of the present invention, the selecting part 130 may provide the laser beam source 110 with the fluorine (F2) gas stored in the third gas storage unit 124 when the photoresist film S is responsive to a laser beam having a wavelength of about 157 nm.

The laser beam source 110 generates a laser beam when the laser beam source 110 is provided with a source gas (step S220).

For example, the source gas may be injected into the discharge tube, and then a high voltage may be applied to the discharge tube. The electrons of the source gas are excited when the high voltage is applied to the discharge tube. Light having a predetermined wavelength is generated when the excited electrons return to a stable state. The light having the predetermined wavelength is reflected by the mirror and the half-mirror so that the light moves between the mirror and the half-mirror. The half-mirror reflects some light and transmits the remaining light so that the light transmitted by the half-mirror is emitted from the laser beam source 110.

In some embodiments of the present invention, the X-ray generating unit 108 may generate an X-ray beam according to the control of the controller 104. For example, the cathode part 140 may emit electrons and the grid electrode part 150 may accelerate the electrons emitted from the cathode part 140. The focus electrode part 160 concentrates the electrons accelerated by the grid electrode part 150 and the concentrated electrons hit the target part 170. The electrons hitting the target part 170 generate X-ray beams and heat. The X-ray beams are emitted from the X-ray generating unit 108 through a window formed in a surface of the X-ray generating unit 108 which faces the control unit 109.

The control unit 109 controls a path of the laser beam or the X-ray beam, so that the laser beam or the X-ray beam is irradiated onto only the photoresist film S.

Changes and properties of components in the photoresist film S are analyzed while the laser beam or the X-ray beam is irradiated onto the photoresist film S.

Referring to FIG. 4, the infrared source part 180 irradiates the infrared light onto the photoresist film S which is exposed to the laser beam or the X-ray beam (step S310).

Some infrared light irradiated onto the photoresist film S passes through the photoresist film S and is detected by the detecting part 190 (step S320).

The processing part 200 processes operations in response to output signals provided from the detecting part 190 to analyze the changes of the components and the properties of the photoresist film S.

In the method of analyzing the photoresist film, light selected in accordance with the type of the photoresist film S may be irradiated onto the photoresist film S, and the changes and properties of components in the photoresist film S. which are caused by exposing the photoresist film S to the light, may be instantly analyzed.

According to some embodiments of the present invention, light that is selected and generated in accordance with the type of a photoresist film S may be irradiated onto the photoresist film S. In addition, changes and properties of components in the photoresist film S may be analyzed while the exposure process of the photoresist film S is being performed.

The foregoing is illustrative of the present invention and is not to be construed as limiting thereof. Although a few example embodiments of the present invention have been described, those skilled in the art will readily appreciate that many modifications are possible in the example embodiments without materially departing from the novel teachings and advantages of this invention. Accordingly, all such modifications are intended to be included within the scope of the present invention as defined in the claims. In the claims, means-plus-function clauses are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The present invention is defined by the following claims, with equivalents of the claims to be included therein.

What is claimed is:

1. An apparatus for analyzing photoresist film, comprising:
   a light generator configured to generate light having various wavelengths and to irradiate the generated light onto a photoresist film, the light generator comprising:
   a laser generating unit configured to generate laser beams having a wavelength in an ultraviolet light range;
   an X-ray generating unit configured to generate X-ray beams; and a control unit configured to control a path of light generated by the laser generating unit and the X-ray generating unit so that the light is irradiated onto only the photoresist film within the chamber;

a controller configured to select light having a wavelength which is responsive to the photoresist film; and an infrared spectroscope configured to analyze changes and properties of components in the photoresist film caused by exposing the photoresist film to the selected light;

wherein the laser generating unit comprises:

a plurality of gas storage parts storing a plurality of laser source gases;

a laser beam generating part generating laser beams using the laser source gases and irradiating the laser beams onto the photoresist film; and a selecting part connected to the gas storage parts and laser beam generating part to provide the laser beam generating part with one of the laser source gases.

2. The apparatus of claim 1, wherein the gas storage parts respectively store argon fluoride (ArF) gas, krypton fluoride (KrF) gas and fluorine (F2) gas.

3. The apparatus of claim 1, wherein the X-ray generating unit comprises:

a cathode configured to emit electrons;

a grid electrode configured to control the electrons emitted from the cathode; and a target to which the electrons are caused to collide so that X-ray beams are generated.

4. An apparatus for analyzing photoresist film, comprising:

a light generator configured to generate light having various wavelengths and to irradiate the generated light onto a photoresist film, the light generator comprising:

a laser generating unit configured to generate laser beams having a wavelength in an ultraviolet light range; and a control unit configured to control a path of light generated by the laser generating unit so that the light is irradiated onto only the photoresist film within the chamber;

a controller configured to select light having a wavelength which is responsive to the photoresist film; and an infrared spectroscope configured to analyze changes and properties of components in the photoresist film caused by exposing the photoresist film to the selected light;

wherein the laser generating unit comprises:

a plurality of gas storage parts storing a plurality of laser source gases;

a laser beam generating part generating laser beams using the laser source gases and irradiating the laser beams onto the photoresist film; and a selecting part connected to the gas storage parts and laser beam generating part to provide the laser beam generating part with one of the laser source gases.

* * * * *